US008329010B2

(12) United States Patent
Gau (10) Patent No.: US 8,329,010 B2
(45) Date of Patent: Dec. 11, 2012

(54) CHIP ASSAY HAVING IMPROVED EFFICIENCY (75) Inventor: Jen-Jr Gau, Pasadena, CA (US)

(73) Assignee: Kotura, Inc., Monterey Park, CA (US)

( * ) Notice: Subject to any disclaimer, the term of this patent is extended or adjusted under 35 U.S.C. 154(b) by 1025 days.

(21) Appl. No.: 12/154,971

(22) Filed: May 28, 2008

(65) Prior Publication Data

US 2009/0011952 A1 Jan. 8, 2009
US 2012/0190584 A9 Jul. 26, 2012

Related U.S. Application Data (63) Continuation-in-part of application No. 09/848,727, filed on May 3, 2001, now Pat. No. 7,399,585.

(60) Provisional application No. 60/201,603, filed on May 3, 2000, provisional application No. 60/958,277, filed on Jul. 2, 2007.

(51) Int. Cl.
*A61B 5/00* (2006.01)

(52) U.S. Cl. ........... 204/403.13; 204/403.01; 205/777.5; 205/780

(58) Field of Classification Search .................. 204/409, 204/450, 453, 454, 600, 604, 403.01–403.15; 205/777.5, 778, 792
See application file for complete search history.

(56) References Cited

U.S. PATENT DOCUMENTS

2002/0123048 A1* 9/2002 Gau .................................. 435/6
2005/0106570 A1* 5/2005 Kataoka et al. ..................... 435/6

FOREIGN PATENT DOCUMENTS

WO WO 03/051506 A1 * 6/2003

OTHER PUBLICATIONS

Gau et al. Biosensors & Bioelectronics 16 (2001) 745-755.*
Sun et al. Talanta 47 (1998) 487-495.*

* cited by examiner

*Primary Examiner* — Jeffrey T Barton
*Assistant Examiner* — Steven Rosenwald
(74) *Attorney, Agent, or Firm* — Gavrilovich, Dodd & Lindsey, LLP (57) ABSTRACT The chip includes electrodes on a substrate. The electrodes include a working electrode, a reference electrode, and a counter electrode. The reference electrode is constructed so as to not have an intrinsic potential. A self-assembly monolayer is positioned on the reference electrode. The self-assembly monolayer includes spacers and active probes. The active probes are configured to have a higher affinity for a capture probe than the spacers have for the capture probe.

13 Claims, 10 Drawing Sheets

CHIP ASSAY HAVING IMPROVED EFFICIENCY

RELATED APPLICATIONS

This application is a continuation-in-part of U.S. patent application Ser. No. 09/848,727, filed on May 3, 2001, entitled "Biological Identification System with Integrated Sensor Chip," published as U.S. Patent Publication No. US2002/0123048, and issued as U.S. Pat. No. 7,399,585 which claims the benefit of U.S. Provisional Patent Application Ser. No. 60/201,603, filed May 3, 2000; and this Application claims the benefit of U.S. Provisional Patent Application Ser. No. 60/958,277, filed on Jul. 2, 2007, entitled "Chip Assay Having Improved Efficiency," and incorporated herein in its entirety.

BACKGROUND

1. Field of the Invention

The invention relates to assays and more particular to sensors for use with assays.

2. Background of the Invention

A variety of assays can be performed using an assay chip that includes one or more sensors positioned on a substrate. Each of the sensors can include a working electrode, a reference electrode, and a counter electrode positioned on the substrate. The reference electrode typically includes or consists of two metal layers that contact each other so the reference electrode has an intrinsic potential against which the potential of other electrodes can be measured.

In some instances, the reference electrode is made with a single layer of metal in order to reduce challenges associated with manufacturing the reference electrode. However, these sensors are often produce inconsistent results because the potential of the reference electrode can float. As a result, there is a need for a manufacturable sensor that can provide consistent results.

SUMMARY OF THE INVENTION

The chip includes electrodes on a substrate. The electrodes include a working electrode, a reference electrode, and a counter electrode. The reference electrode is constructed so as to not have an intrinsic potential. A self-assembly monolayer is positioned on the reference electrode. The self-assembly monolayer includes spacers and active probes. The active probes are configured to have a higher affinity for a capture probe than the spacers have for the capture probe.

DETAILED DESCRIPTION OF THE PREFERRED EMBODIMENT

A chip sensor has one or more sensors on a substrate. The sensors each include a working electrode, a reference electrode, and a counter electrode on a substrate. The reference electrode is constructed without an intrinsic potential. For instance, the reference electrode can include a single layer of a metal. A self-assembly monolayer is on at least the reference electrode and/or at least the working electrode.

The self-assembly monolayer is a heterogeneous self-assembly monolayer includes spacers between active probes. The active probes are configured to have a higher affinity for a capture probe than the spacers. As a result, the capture probe preferentially bonds to the active probes over the spacers. The capture probe bonds to the target agent being sought by the assay. Accordingly, the active probes take part in connecting the target agent to the electrodes but the spacers do not connect the target agent to the electrodes. The inventors have found that the presence of the spacers between the active probes increases the impedance of the reference electrode and accordingly stops or reduces floating of the reference electrode potential during the operation of the sensor.

The spacers can also reduce signal to noise ration in the assay results. For instance, some instances of the assay determine the presence of the target agent through by measuring current through the working electrode that results from a reaction between a mediator and the working electrode. As a result, sources of current at the working electrode that are not from the mediator are a source of noise in the assay results. The inventors have found that a self-assembly monolayer that includes spacers on the working electrode can act as a dielectric layer on the working electrode. As a result, the self-assembly monolayer can prevent sources of current that are from sources other than the mediator from passing through the working electrode. However, the same self-assembly monolayer permits the redox reaction between the mediator and the working electrode to continue. One possible explanation for the continued redox reaction between the mediator and the working electrode is that the mediator can get caught in the self-assembly monolayer and permit signal tunneling through the self-assembly monolayer.

Because a self-assembly monolayer that includes spacers and active probes can stop or reduce floatation of the reference electrode potential and/or reduce the signal to noise ration in the assay results, the self-assembly monolayer increases the consistency and/or efficiency of the result provided by the sensor.

Figure 1A:
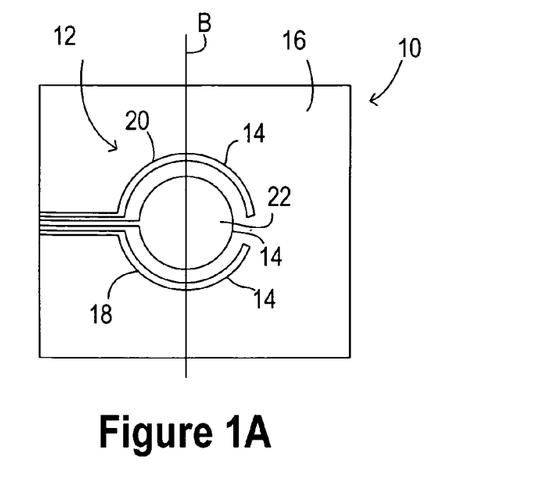
FIG. 1A is a topview of an assay chip having a sensor for detecting the presence and/or amount of a target agent.
Figure 1B:
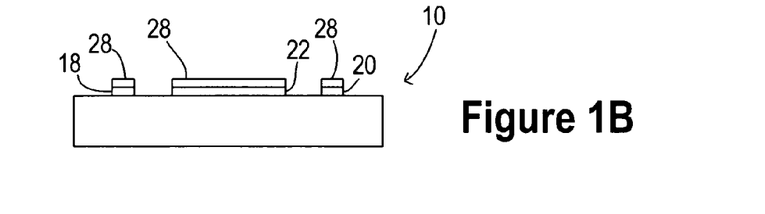
FIG. 1B is a cross section of the assay chip illustrated in FIG. 1A taken along the line labeled B.

FIG. 1A and FIG. 1B illustrate an example of a portion of an assay chip 10 having a sensor 12. FIG. 1A is a topview of the chip 10 and FIG. 1B is a cross section of the chip 10 shown in FIG. 1A taken at the line labeled B. The chip 10 includes a plurality of electrodes 14 positioned on a substrate 16. A suitable substrate 16 includes, but is not limited to, a silicon substrate 16. Although the substrate 16 is shown as being constructed from a single material, the substrate 16 can have a composite construction.

The electrodes 14 include a reference electrode 18 and a counter electrode 20 positioned adjacent to a working electrode 22. In some instances, the counter electrode 20 and the reference electrode 18 are positioned on opposing sides of the working electrode 22. The counter electrode 20 and the reference electrodes 18 can have the same shape or can have different shapes. The counter electrode 20 and/or the reference electrode 18 can be positioned such that a portion of the working electrode 22 is positioned between different regions of the counter electrode 20 and/or between different regions of the reference electrode 18. Although the working electrode 22 is shown as having a round shape, the working electrode 22 can have a variety of other shapes including, but not limited to, rectangular shapes.

The reference electrode 18 can include a single layer of a conductive material such as a metal. For instance, the reference electrode can consist of a single layer of a metal such as gold, silver, copper, platinum, chromium, aluminum, titanium and nickel. The working electrode 22, the counter electrode 20, and the reference electrode 18 can be constructed of the same material or from different materials. Other suitable electrodes 14 include, but are not limited to, gold silver, copper, platinum, chromium, aluminum, titanium and nickel.

The working electrode 22 can be constructed such that the largest dimension of the working electrode 22 is less than 4 mm, 1 mm, 100 µm or 50 µm. Suitable widths for the counter electrode 20 and the reference electrode 18 include, but are not limited to, widths less than 20 µm, 100 µm, 0.5 mm or 3 mm. Suitable dimensions for the gap between the working electrode 22 and the reference electrode 18 and/or between the working electrode 22 and the counter electrode include, but are not limited to, gaps less than 1 µm, 100 µm, 0.5 mm or 2 mm. These dimensions can provide for a sensor 12 having a compact size that is suitable for use in on site assay equipment.

The working electrode 22 includes an adhesion layer 28. As will be described in more detail below, a portion of a test probe can have a larger affinity for the adhesion layer 28 than for the working electrode 22. As a result, the adhesion layer 28 can increase the affinity of a portion of the test probe 40 for the working electrode 22.

Figure 1C:
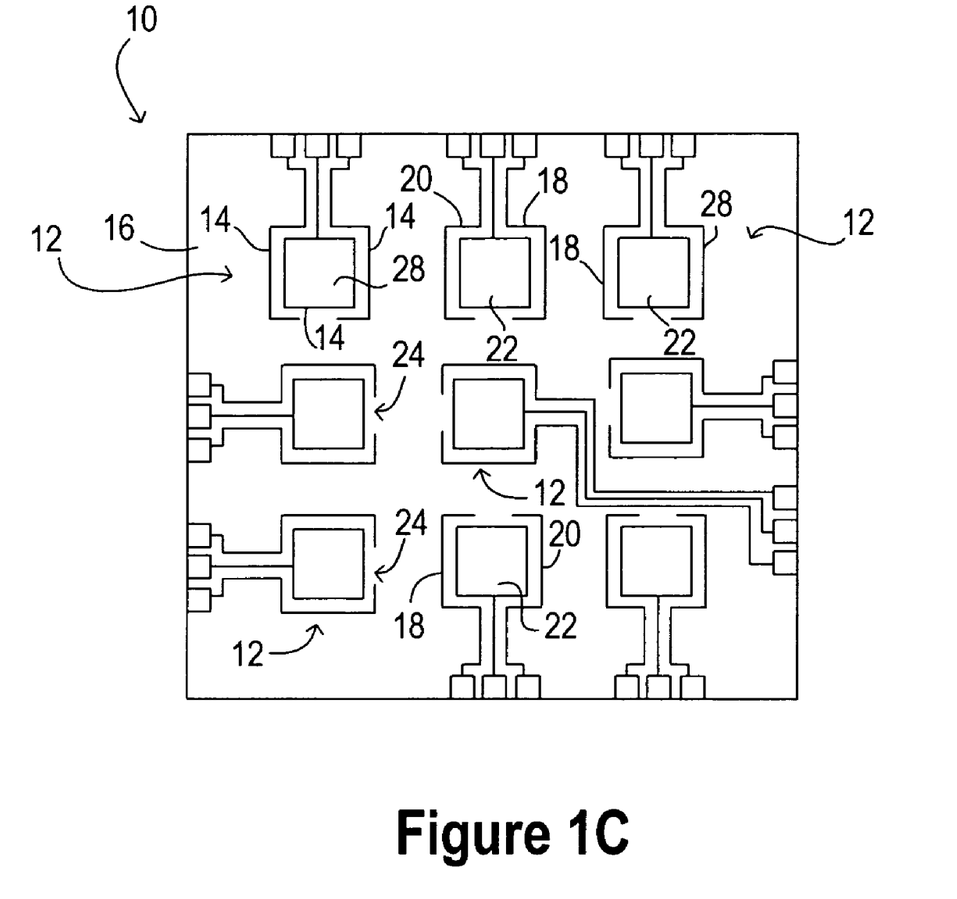
FIG. 1C illustrates an assay chip having a plurality of sensors.

Although FIG. 1A and FIG. 1B illustrate the chip 10 as having a single sensor 12, a chip 10 can include a plurality of sensors 12 as illustrated in FIG. 1C. The sensors 12 can be arranged in an array on the chip 10. Each of the sensors 12 includes a working electrode 22, a reference electrode 18 and a counter electrode 20. Different sensors 12 on the chip 10 can be employed concurrently or serially. Each sensor 12 can be employed to test for the presence of a different target agent. As a result, the chip 10 can provide highly efficient testing for a plurality of different target agents. Alternatively, multiple sensors 12 can be employed to test for the presence of the same target agent. The multiple tests can serve as a redundancy check or the tests performed on each sensor 12 can be for target agents from different sources.

Figure 2:
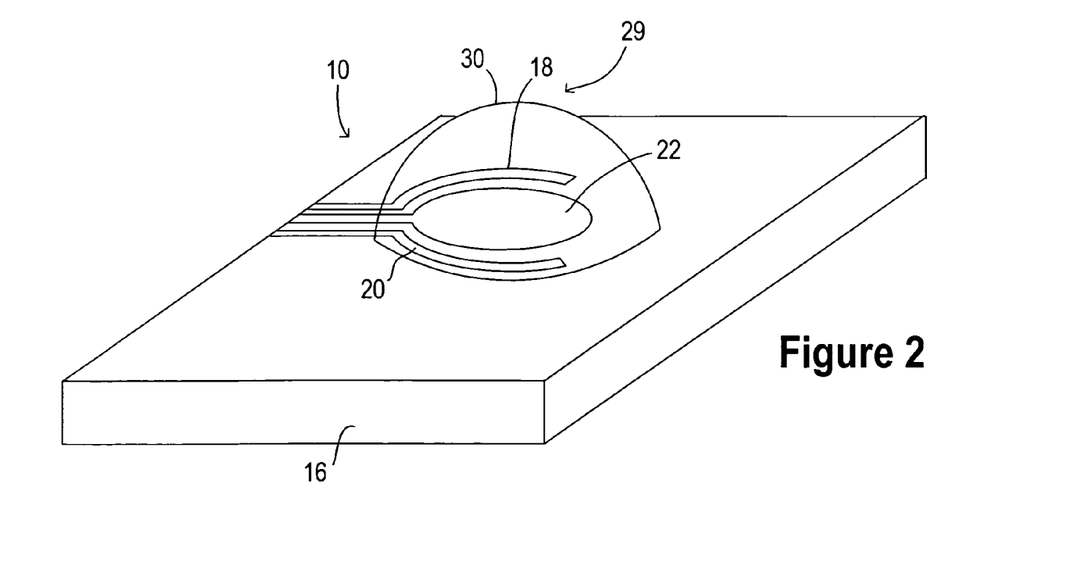
FIG. 2 illustrates a sensor system having a test volume positioned on the sensor of FIG. 1A.

A sensor system 29 is formed during operation of the chip 10 as illustrated in FIG. 2. Although the adhesion layer 28 is present on at least one of the electrodes, the adhesion layer 28 is not illustrated in FIG. 2. The sensor system 29 includes a test volume 30 positioned on the sensor 12. The test volume 30 is concurrently positioned over the working electrode 22, the reference electrode 18 and the counter electrode 20. In some instances, surface tension preserves the shape of the test volume 30 as well as to keep the test volume 30 positioned over the electrodes 14.

Figure 3A:
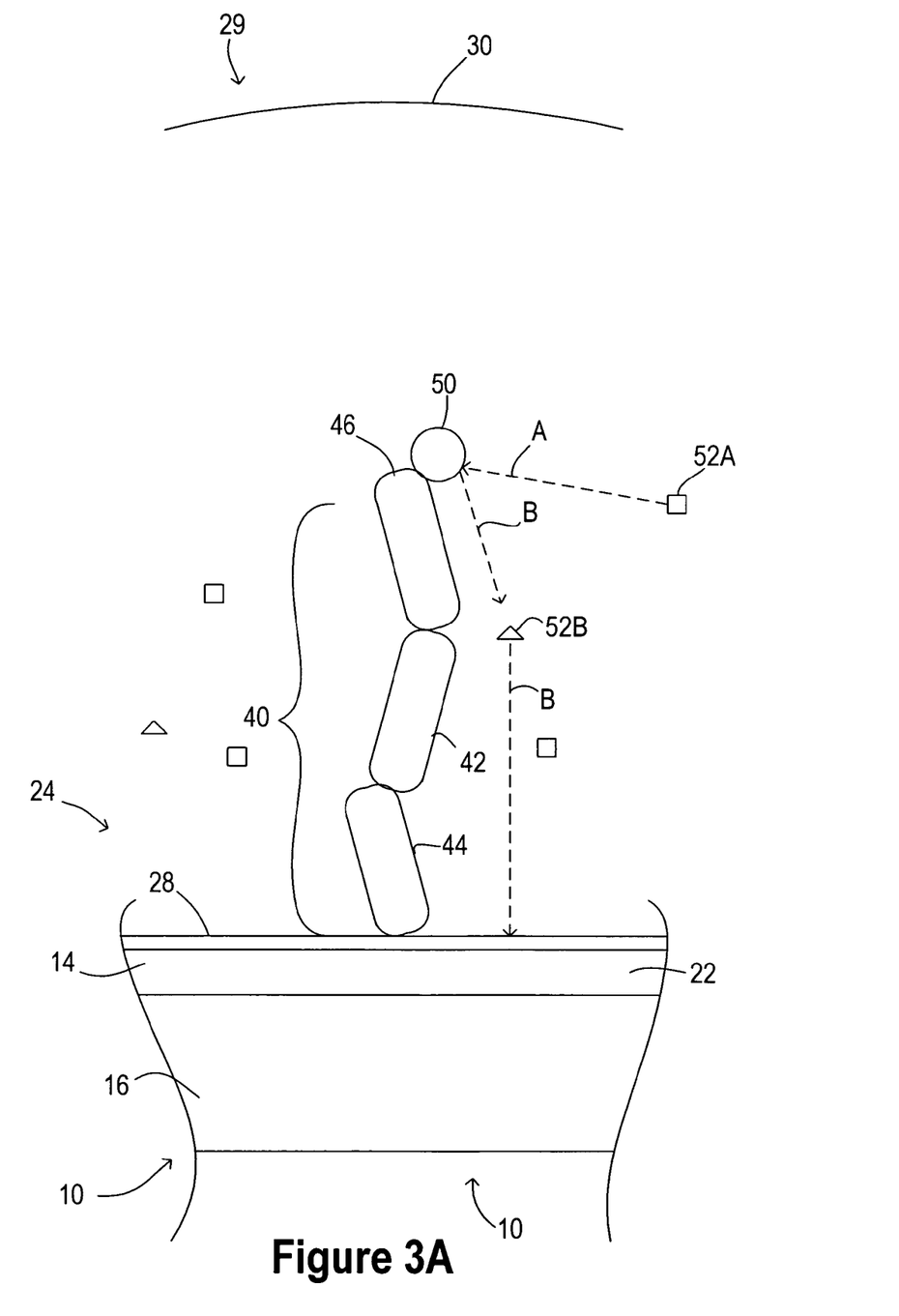
FIG. 3A illustrates a generalized example of an assay that is suitable for use with the assay chip illustrated in FIG. 1A. The assay employs an adhesion layer to bond a test probe to the working electrode. The adhesion layer has a higher affinity for a capture probe than the working electrode has for the capture probe.

FIG. 3A provides a generalized example of a sensor system 29 according to FIG. 2. FIG. 3A is a portion of a cross section of the sensor system 29 illustrated in FIG. 2.

The sensor system 29 includes a test probe 40 bonded to the adhesion layer 28 on a working electrode. A single test probe 40 is shown for the purposes of illustration; however, the density of the test probes 40 across the working electrode 22 is generally much higher. The test probe 40 includes a portion of a target agent 42 between a capture probe 44 and a signaling probe 46. The assay indicates the presence of the target agent 42. Suitable target agents 42 include, but are not limited to, polysaccharides, nucleic acids, cells and strands of genetic materials such as DNA or RNA and antibodies.

The adhesion layer 28 can increase the affinity of the capture probe 44 for the working electrode 22 above the affinity the capture probe 44 has for the working electrode 22 without the adhesion layer 28. The capture probe 44 serves to link the working electrode 22 to the target agent 42. As will become evident below, suitable capture probes 44 include, but are not limited to, deoxyribonucleic acids (DNA), ribonucleic acids (RNA), peptide nucleic acids (PNA), locked nucleic acids (LNA) and proteins such as antibodies.

A reporter 50 is bonded to the signaling probe 46. The signaling probe 46 is configured to link the target agent 42 with the reporter 50. At least one mediator 52 is in the testing volume. The mediator 52 and the reporter 50 can each exist in more than one state in the test volume 30. Examples of different states include different states of oxidation.

During operation of the chip 10, the chip 10 is in electrical communication with electronics (not sown) configured to apply a potential between the working electrode 22 and the reference electrode 18 of a sensor 12 while monitoring current passing through a circuit that includes the working electrode 22, the test volume 30 and the counter electrode 20 of that circuit.

The mediator 52 and the reporter 50 interact such that the mediator 52 converts from a first mediator state 52A to a second mediator state 52B and the reporter 50 converts from a first reporter state to a second reporter state. The dashed line labeled A illustrates the first mediator state 52A diffusing to the reporter 50 where it is converted to the second mediator state 52B. The dashed lines labeled B illustrate the second mediator state 52B diffusing through the test volume 30 to the working electrode 22. The potential applied between the working electrode 22 and the reference electrode 18 is raised to a level that causes electron transfer to occur between the working electrode 22 and the second mediator state 52B. The electron transfer allows current to flow through a circuit that includes the working electrode 22, the test volume 30 and the counter electrode 20. As a result, a current flowing through the working electrode 22 and the counter electrode 20 indicates that the mediator 52 is being converted from the first mediator state 52A to the second mediator state 52B.

As will be evident below, the reporter 50 is not present in the test volume 30 when the target agent 42 is not present. When the reporter 50 is not present, the mediator 52 is not converted from the first mediator state 52A to the second mediator state 52B. As a result, the current through the working electrode is not present when the target agent 42 is not present in the test volume 30. Because the current is present when the target agent 42 is present but is not present when the target agent 42 is not present, the current indicates the presence of the target agent 42 in the test volume 30.

Figure 3B:
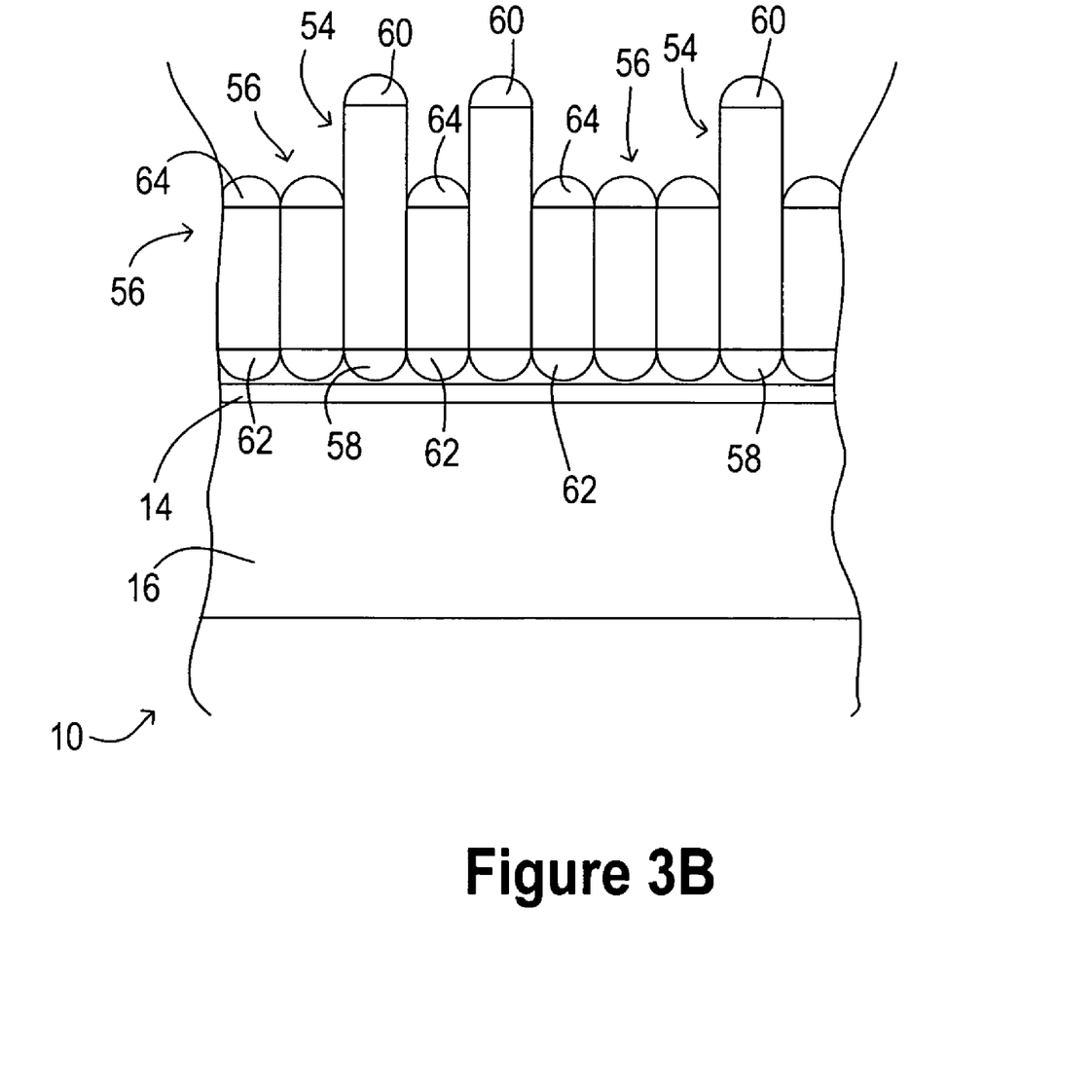
FIG. 3B illustrates a heterogeneous self-assembly monolayer suitable for serving as an adhesion layer.

FIG. 3B is a cross section of a sensor that includes an adhesion layer 28 on an electrode 14. The illustrated adhesion layer 28 and electrode 14 can represent the arrangement on the working electrode, the reference electrode, and/or the counter electrode. The adhesion layer 28 includes or consists of a self-assembly monolayer that has more affinity for the capture probe 44 than the electrode 14 has for the capture probe 44 when the self-assembly monolayer is not present on the electrode 14.

A self-assembly monolayer is a two-dimensional film, one molecule thick, where each molecule is covalently bonded to a surface. The classical example of a self-assembly monolayer is the reaction of alkanethiols with a gold surface. Functionalized silane compounds can also self-assemble on silicon surfaces. Since molecules that are not bound directly to the surface can normally be washed away, self-assembly monolayers can provide a one molecule thick film immobilized on the surface.

The illustrated self-assembly monolayer is a heterogenous self-assembly monolayer that includes different compounds in the self-assembly monolayer. For instance, the illustrated self-assembly monolayer includes active probes 54 and spacers 56. The active probes 54 include an electrode linker 58. The electrode linker 58 is configured to link the active probes 54 to the electrode 14. The active probes 54 also include a probe linker 60. The probe linker 60 is configured to link the active probe 54 to the capture probe 44. For instance, the probe linker can include one or more binding sites that are each configured to bind the capture probe. In some instances, the probe linker 60 is positioned at the terminal end of the active probes 54.

The spacers 56 each include an electrode linker 62 configured to link the spacers 56 to the electrode 14. The spacers 56 also include a terminal end 64. The terminal end 64 has less affinity for the capture probes 44 than the probe linker 60 has for the capture probes 44. In some instance, the terminal end 64 is configured such that the spacer 56 does not have substantial affinity for the capture probes 44. Accordingly, the capture probes 44 bond to the active probes 54 rather than the spacers 56.

Figure 3C:
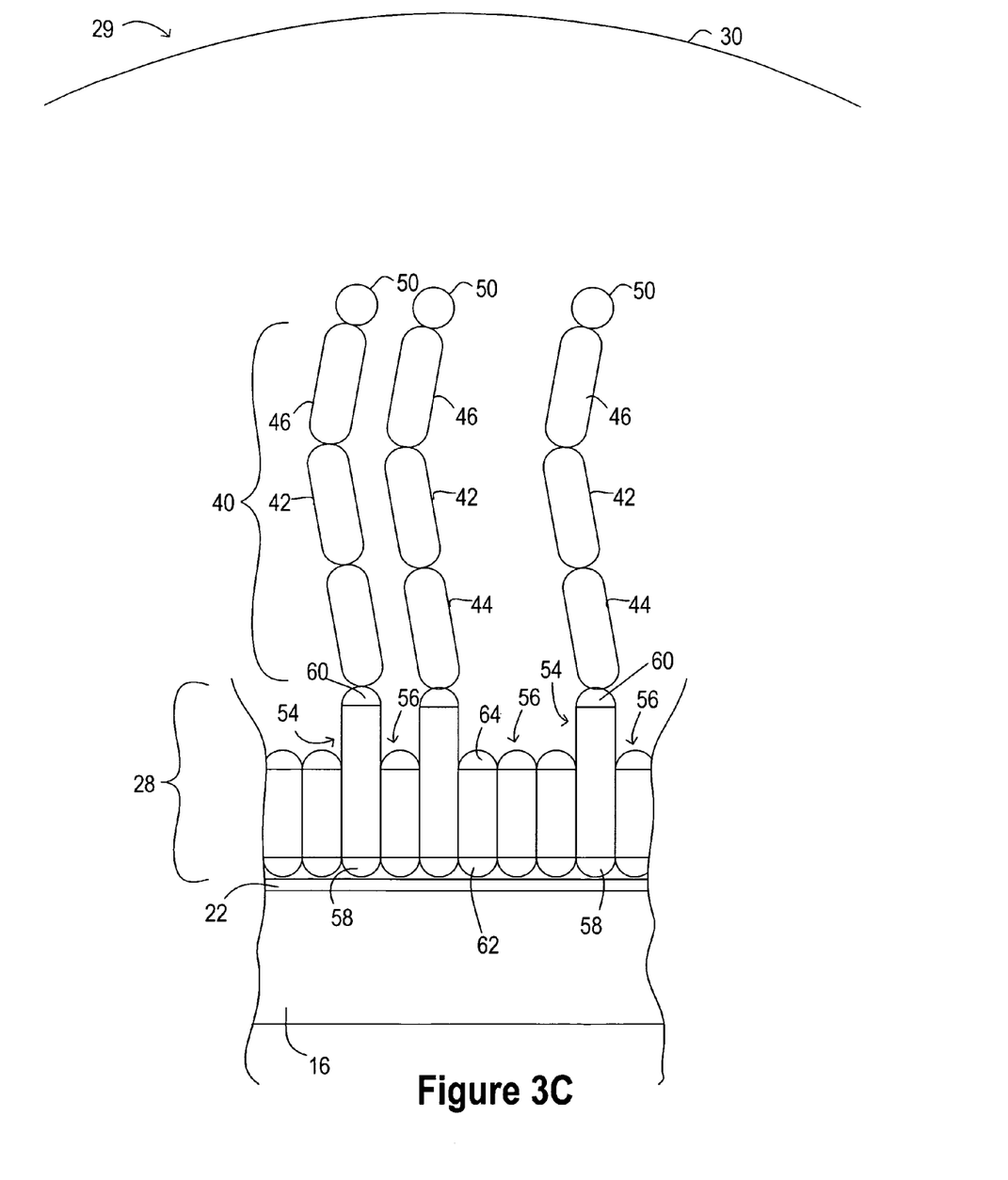
FIG. 3C illustrates the heterogeneous self-assembly monolayer of FIG. 3B used in conjunction with the test probes of FIG. 3A.

FIG. 3C illustrates the sensor of FIG. 3A used in conjunction with the test probe and reporter of FIG. 3B. The active probes 54 are linked to the test probes while the spacers 56 are not linked to test probes.

Each of the compounds that serve as an active probe 54 can be the same or the active probes 54 can include a plurality of different compounds that each serve as an active probe 54. Each of the compounds that serve as a spacer 56 can be the same or the spacers 56 can include a plurality of different compounds that each serve as a spacer 56. The ratio of spacers 56 to active probes 54 in the self-assembly monolayer can affect the performance of an assay. The ratio of spacers 56 to active probes 54 is preferably in a range of 100:1 to 1:100, or 10:1 to 1:10 or 5:1 to 1:5.

Suitable electrode linkers 58 for use with the active probes 54 include, but are not limited to, thiol groups. As a result, the active probes 54 can be thiolated active probes 54. When a thiolated active probe is linked to the electrode 14, the thiolated active probe includes a sulfur that is directly linked to the electrode 14. A thiol electrode linker 58 is suitable for use as the electrode linker 58 when the electrode surface includes or consists of gold.

Suitable electrode linkers 62 for use with the spacers 56 include, but are not limited to, thiol groups. As a result, the active probes 54 can be thiolated spacers 56. When a thiolated spacer is linked to the electrode 14, the thiolated spacer includes a sulfur that is directly linked to the electrode 14. A thiol electrode linker 62 is suitable for use as the electrode linker 62 when the electrode surface includes or consists of gold. The electrode linker 62 employed in the spacers 56 can be the same or different from the electrode linker 62 employed for the active probes 54.

The probe linkers 60 can depend on the structure of the capture probe 44. Examples of probe linkers 60 include, but are not limited to, groups such as hydroxyl groups (—OH), amine groups (—NH$_2$, NHR where R can represent an organic group such as an alkyl group), and compounds that include these groups. Examples of terminal ends 64 for the spacers 56 include, but are not limited to, alkyl groups and other groups such as hydroxyl groups (—OH) and amine groups (—NH$_2$, NHR where R can represent an organic group such as an alkyl group). The terminal end 64 of the spacers 56 can be different from the probe linker 60. For instance, when the probe linker 60 is an amine, the terminal end 64 of the spacers 56 can be a hydroxyl group.

In some instances, the active probes 54 can be constructed such that the probe linker 60 is positioned above the terminal ends 64 of the spacers 56. For instance, the active probes 54 can be longer than the spacers 56. As a result, the probe linker 60 can readily bond with a capture probe 44 included in a solution positioned on the sensor.

Suitable active probes 54 include one or more alkylene moieties. Each of the alkylene moieties can have a backbone with one or more carbons, two or more carbons, three or more carbons, or four or more carbons. For instance, the active probes 54 can include one or more moieties represented by —(CH$_2$)$_n$— where n is 1 or more, 2 or more, 3 or more or 4 or more. One or more of the alkylene moieties in the active probe 54 can be substituted and/or branched. For instance, a suitable active probe 54 can include one or more alkylene moieties that are fully or partially halogenated. When an active probe 54 includes a plurality of alkylene moieties, different alkylene moieties can be linked together by an ether linkage (—O—), a thioether linkage (—S—), an amine linkage (—NR— where R is a hydrogen or an organic group such as an alkyl group), a ketone linkage (—CO—), an ester link (—CO—O—), a thioester link (—S—CO—), or an amide linkage (—CO—NH).

Suitable spacers 56 include one or more alkylene moieties. Each of the alkylene moieties can have a backbone with one or more carbons, 2 or more carbons, 3 or more carbons, or 4 or more carbons. For instance, the spacers 56 can include one or more moieties represented by —(CH$_2$)$_n$— where n is 1 or more, 2 or more, 3 or more or 4 or more. One or more of the alkylene moieties in the spacer 56 can be substituted and/or branched. For instance, a suitable spacer 56 can include one or more alkylene moieties that are fully or partially halogenated. When a spacer 56 includes a plurality of alkylene moieties, different alkylene moieties can be linked together by oxygen (—O—), a thioether linkage (—S—), an amine linkage (—NR— where R is a hydrogen or an organic group such as an alkyl group), a ketone linkage (—CO—), or an ester link (—COO—).

Figure 4:
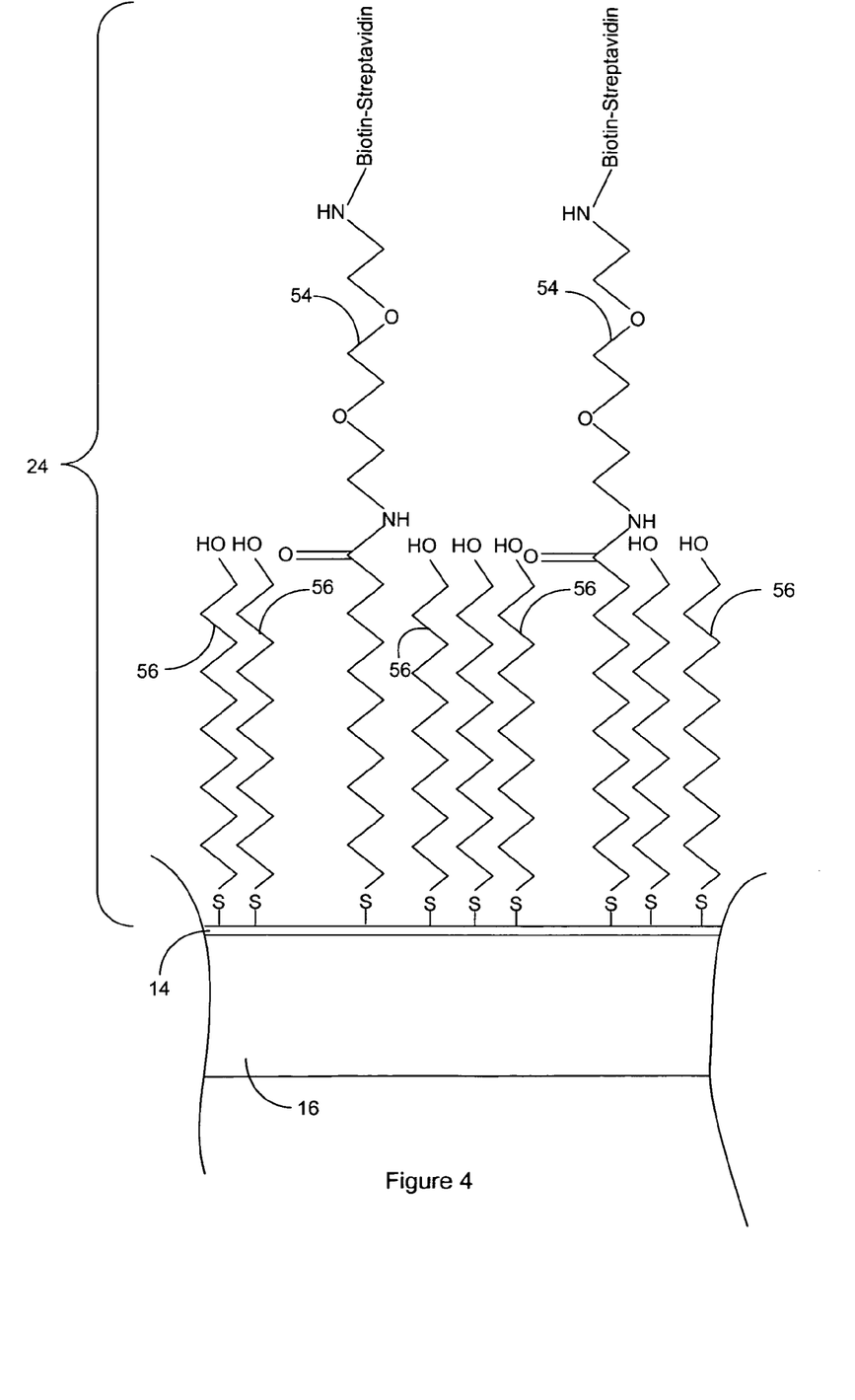
FIG. 4 illustrates a sensor having a self-assembly monolayer that includes active probes with streptavidin bonded to DAD-C12-SH (12-mercapto(8-biotinamide-3,6-dioxaoctyl) dodecanamide) and 11-mercapto-1-undecanol as spacers.

An example of a suitable active probe 54 includes, but is not limited to, a substituted biotin, substituted biotin bonded to streptavidin, dextran, and MUDA (mercaptoundecanoic acid). For instance, when the assay is employed to identify the presence of genetic materials such as DNA or RNA and the electrode 14 to which the active probe 54 is to be bonded is gold, a suitable active probe 54 includes a biotinylated thiol bonded to streptavidin. An example of a suitable biotinylated thiol includes, but is not limited to, DAD-C12-SH (12-mercapto(8-biotinamide-3,6-dioxaoctyl)dodecanamide). An example of a suitable spacer 56 includes, but is not limited to, thiols and hydroxylated thiols such as 6-mercapto-1-hexanol. FIG. 4 shows a sensor having a self-assembly monolayer that includes active probes 54 with streptavidin bonded to DAD-C12-SH (12-mercapto(8-biotinamide-3,6-dioxaoctyl)dodecanamide) and 11-mercapto-1-undecanol as spacers 56. The streptavidin includes several probe linkers represented by a binding loop (residues 45 to 52) that serve as binding cites for a biotinylated capture probe.

Figure 5A:
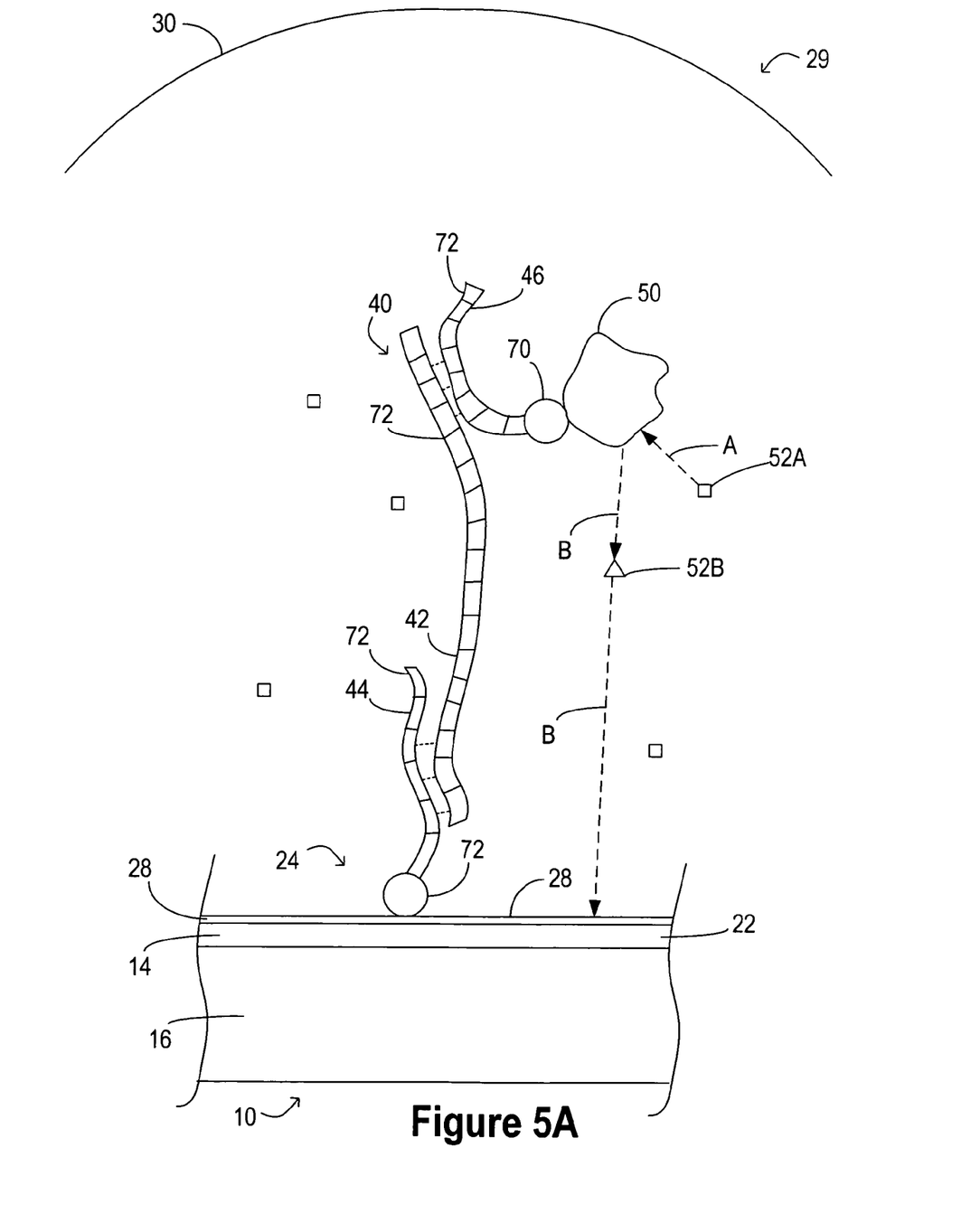
FIG. 5A illustrates the assay of FIG. 3A adapted for detecting the presence of a particular strand of genetic material.

FIG. 5A illustrates the test volume 30 illustrated in FIG. 3A adapted for detecting a strand of genetic material 72 such as DNA or RNA. The capture probe 44, the target agent 42, the signaling probe 46 are each strands of genetic material 72. A portion of the capture probe 44 is complementary to a portion of the target agent 42 to provide base pairing between the complementary portions of the capture probe 44 and the target agent 42. A portion of the target agent 42 is complementary to a portion of the signaling probe 46 to provide base pairing between the complementary portions of the target agent 42 and the signaling probe 46.

A suitable reporter 50 for use with the assay components of FIG. 5 includes, but is not limited to, Horseradish Peroxidase (HRP), AP (alkaline phosphotase) and glucose peroxidase. A suitable mediator 52 for use with HRP includes but is not limited to, 3,3',5,5'-tetramethylbenzidine (TMB). A suitable mediator 52 for use with AP includes but is not limited to, niacin derivative (NAD). A suitable mediator 52 for use with glucose peroxidase includes but is not limited to, ruthenium (II) hexamine.

In some instances, the signaling probe 46 is modified to enhance bonding with the reporter 50. For instance, when the reporter 50 includes Horseradish Peroxidase (HRP), one or more bases of the signaling probe 46 can be modified to encourage bonding of the signaling probe 46 to the HRP. For instance, the 5' end of the signaling probe 46 can be modified with fluorescein that can serve as a linker 70 to the HRP.

In some instances, the capture probe 44 is modified with a linker 76 that enhances bonding of the capture probe 44 to the adhesion layer 28. For instance, when the self-assembly monolayer includes streptavidin, the capture probe 44 can be modified with biotin that readily bonds with streptavidin binding sites. In some instances, the 5' end of the capture probe 44 is modified with the biotin.

Figure 5B:
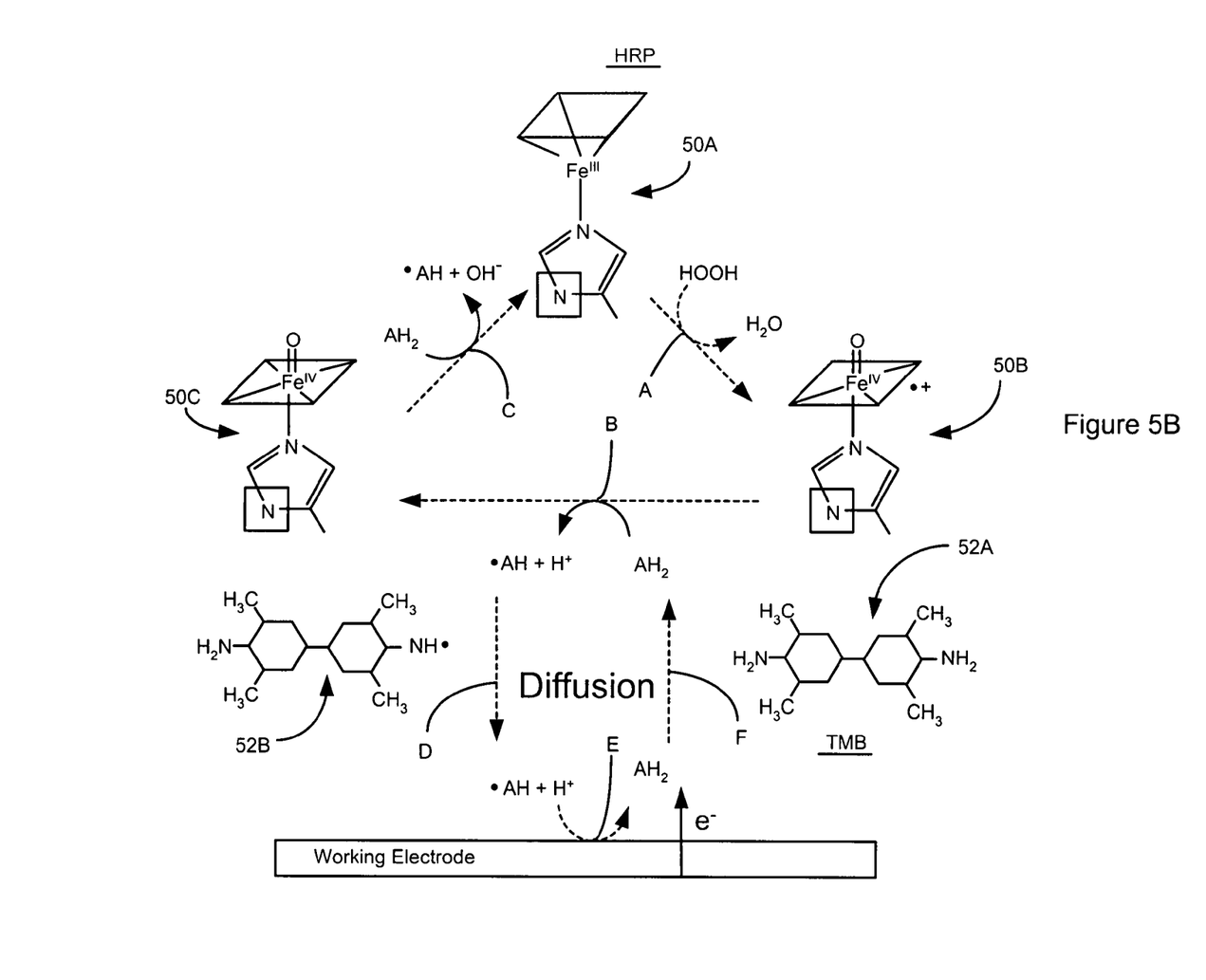
FIG. 5B illustrates a particular example of a reaction mechanism that is suitable for use with the assay illustrated in FIG. 5A.

FIG. 5B illustrates the mechanism of an assay according to FIG. 5A using Horseradish Peroxidase (HRP) as the reporter 50, TMB as the mediator 52 in an aqueous solution including hydrogen peroxide ($H_2O_2$). The mechanism illustrates the HRP existing in a first reporter state 50A, a second reporter state 50B and a third reporter state 50C. The first reporter state 50A is an oxidized state of HRP and the second reporter state 50B is another oxidized state of HRP. The mechanism also illustrates the TMB existing in a first mediator state 52A and second mediator state 52B.

The arrow labeled A illustrates the first reporter state 50A reacting with the hydrogen peroxide to generate the second reporter state 50B. The arrow labeled B illustrates the first mediator state 52A being oxidized by the second reporter state 50B to form the second mediator state 52B. The arrow labeled C illustrates the third reporter state 50C being reduced to form the first reporter state 50A where •AH is the oxidized state of TMB.

The arrow labeled D illustrates the second mediator state 52B diffusing to the working electrode 22. The arrow labeled E illustrates electron transfer occurring at the working electrode 22 so as to return the second mediator state 52B to the first mediator state 52A. The arrow labeled F illustrates the first mediator state 52A diffusing back through the test volume 30 to interact with the second reporter state 50B.

Figure 6:
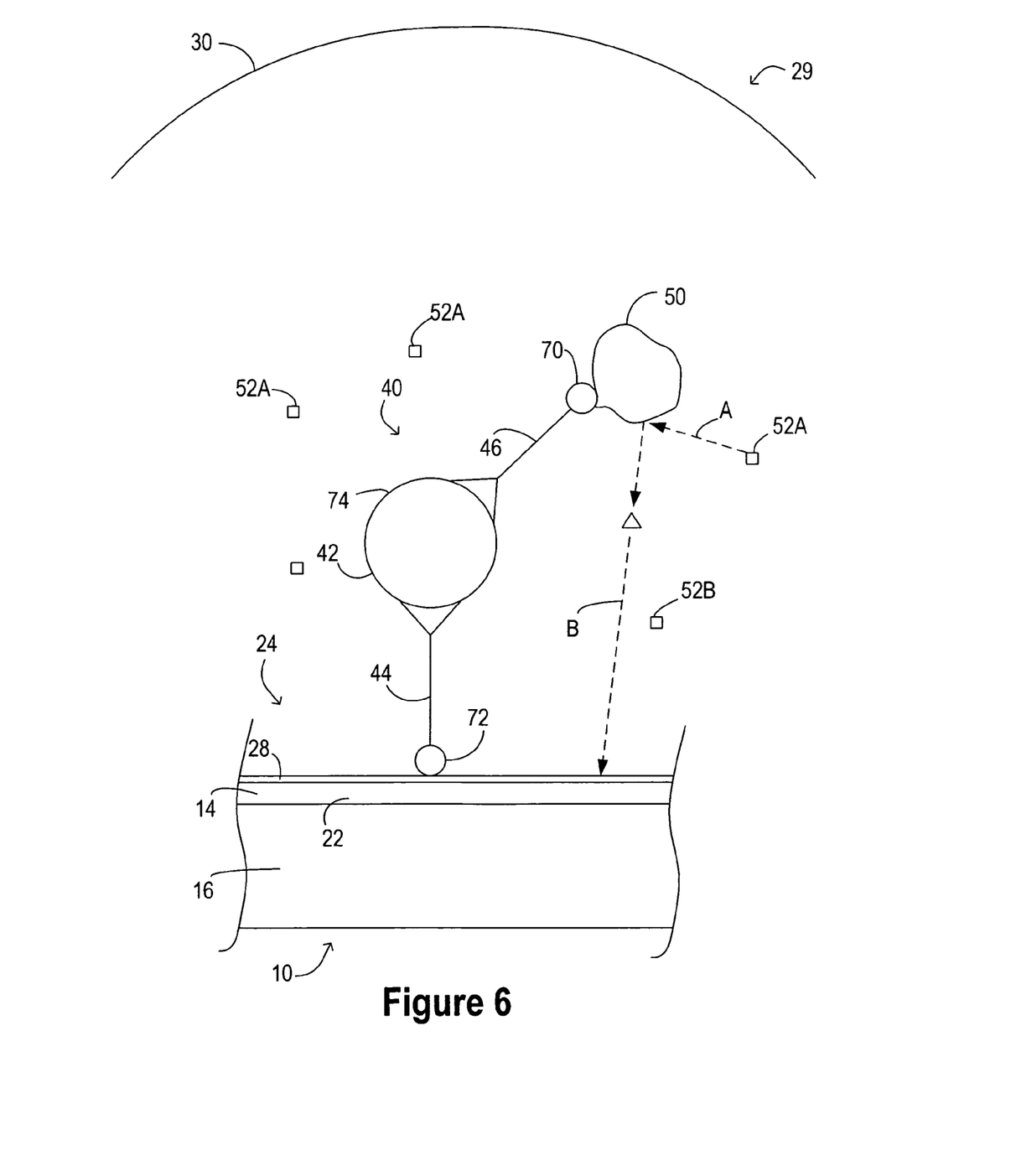
FIG. 6 illustrates the assay of FIG. 3A adapted for detecting the presence of target agents including, but not limited to, proteins and cells.

As illustrated in FIG. 6, the assay illustrated in FIG. 3A can also be adapted for detecting the presence of a cell 74 or a protein. For instance, the capture probe 44 can be the primary antibody of a sandwich assay. Additionally, the signaling probe 46 can be the secondary antibody of the sandwich assay. Suitable target agents 42 for a sandwich assay include, but are not limited to, proteins, polysaccharides and nucleic acids having binding sites specific to the antibody or cells with proteins having binding sites specific to the antibody.

A suitable reporter 50 for use with the assay components of FIG. 6 include, but are not limited to, Horseradish Peroxidase (HRP), AP (alkaline phosphotase) and glucose peroxidase. A suitable mediator 52 for use with HRP includes but is not limited to, 3,3',5,5'-tetramethylbenzidine (TMB). A suitable mediator 52 for use with AP includes but is not limited to, niacin derivative (NAD). A suitable mediator 52 for use with glucose peroxidase includes but is not limited to, ruthenium (II) hexamine.

The primary antibody can be modified to include a linker that enhances bonding to the adhesion layer 28. For instance, when the adhesion layer 28 includes exposed streptavidin, the primary antibody can be modified with biotin that readily bonds with the streptavidin binding sites.

The secondary antibody can be modified to enhance bonding to the reporter 50. For instance, when the reporter 50 includes HRP, the secondary antibody can be modified to encourage bonding of the signaling probe 46 to the HRP. For instance, the secondary antibody can be modified with fluorescein that can serve as a linker 70 to the HRP.

In some instances, the capture probe 44 is modified with a linker 76 that enhances bonding of the capture probe 44 to the adhesion layer 28. For instance, when the self-assembly monolayer includes streptavidin, the capture probe 44 can be modified with biotin that readily bonds with streptavidin binding sites.

The self-assembly monolayer can be synthesized by chemical incubation with sufficient perturbation.

Although the described method forms the self-assembly monolayer on the working electrode, the reference electrode, and the counter electrode, the method can be used to form the self-assembly monolayer on a portion of the electrodes by masking certain electrodes during the formation of the self-assembly monolayer. As a result, the sensor can have a self-assembly monolayer can be on at least the reference electrode or can be on at least the working electrode. The mask can be removed before operation of the sensor. Alternately, after the mask is removed, another self-assembly monolayer can be formed on the previously masked electrode(s). As a result, different self-assembly monolayers can be positioned on different electrodes.

The test volume 30 can be generated on a sensor 12 having a self-assembly monolayer by placing a series of solutions on the working electrode 22. A sample solution is prepared from a sample that may or may not have the target agent 42. When the target agent 42 is located inside cells in the sample or is in the cellular membrane, a lysing agent is added to the sample under suitable lying conditions. The capture probe 44 and the signaling probe 46 are added to the sample solution under conditions that would allow formation of the test probe 40 in the sample solution. The sample solution is applied to the working electrode 22 under conditions that would allow the test probe 40 to bond with the adhesion layer 28. The sample solution can be applied so as to cover the reference electrode 18 and the counter electrode 20. Alternatively, surface tension can be employed to constrain the sample solution to the working electrode 22. The sample solution is then washed from at least the working electrode 22. When the target agent 42 is present in the sample solution, the test probe 40 remains bonded to the active probes 54 in the self-assembly monolayer.

A reporter solution having the reporter 50 is placed on at least the working electrode 22. The reporter solution is placed on the working electrode 22 under conditions that would allow the reporter 50 to bond with the signaling probe 46. The reporter solution can be applied so as to cover the reference electrode 18 and the counter electrode 20. Alternatively, surface tension can be employed to constrain the reporter solution to the working electrode 22. The sensor 12 is then washed with wash solution. The reporter 50 remains bonded to test probes 40 present on at least the working electrode 22 while the remaining reporter 50 is washed away. As a result, the reporter 50 is not present when the target agent 42 is not present in the sample.

A mediator solution having the mediator 52 is placed on the sensor 12 such that the working electrode 22, the reference electrode 18 and the counter electrode 20 are each covered by the mediator solution. The components present on the working electrode 22 and the portion of the mediator solution applied to the working electrode 22 serve as the test volume 30.

Provisional U.S. Patent Application Ser. No. 60/339,766, filed on Nov. 2, 2001, entitled "Integrated Sample Preparation System," and incorporated herein in its entirety; Provisional U.S. Patent Application Ser. No. 60/528,566, filed on Dec. 9, 2003, entitled "Cartridge for use with Electrochemical Sensor," and incorporated herein in its entirety; and Provisional U.S. Patent Application Ser. No. 60/873,078, filed on Dec. 6, 2006, entitled "System for Delivery of Liquid to a Sensor," and incorporated herein in its entirety each discloses a suitable structure for transporting solutions onto the sensor.

EXAMPLE 1

A self-assembly monolayer of 12-mercapto(8-biotinamide-3,6-dioxaoctyl)dodecanamide (biotin-DAD-C12-SH, Roche GmBH, Germany) was formed on a gold surface. The bare gold surface was cleaned and incubated for 18 hours in a 50 mM solution of biotin-DAD-C12-SH in ethanol with 4.5E-4M 11-mercapto-1-undecanol (Aldrich Chemical Co., 44, 752-8). The result was rinsed with ethanol and water.

EXAMPLE 2

The active probes and capture probes were formed on a self-assembly monolayer. Each working electrode was incubated with 2.5 μL of 100 mM N-hydroxysuccinimide and 400 mM N-3-dimethylaminopropyl-N-ethylcarbodiimide for 10 min. The sensors were incubated in biotin (5 mg/ml in 50 mM sodium acetate; Pierce, Rockford, Ill.) for 10 min. The biotinylated sensors were incubated in 4 μL of 0.5 U/ml of streptavidin in RNase-free H2O (catalog no. 821739; MP Biomedicals, Aurora, Ohio) for 10 min. The streptavidin-coated sensors were incubated with biotinylated capture probes (4 μL; 1 μM in 1 M phosphate buffer, pH 7.4) for 30 min.

EXAMPLE 3

The active probes and capture probes were formed on a self-assembly monolayer constructed according to Example 1. A test volume was formed on the sensor and tested for a target agent. A mixture of N-hydroxysuccinimide and 1-ethyl-3-(3-dimethylaminopropyl)carbodiimide were placed in a vial and vortexed. Each working electrode was covered with the mixture. The mixture was incubated on the sensor at room temperature for 10-15 min in a covered, humidified glass Petri dish. At the completion of the incubation period, the sensor chip was rinsed with de-ionized water, dried with nitrogen, and then place the sensor chip back in the Petri dish.

A capture probe solution was made with a monoclonal antibody capture probe in phosphate buffer solution (PBS) at a concentration ranging from 0.01 to 1 mg/mL depending on the purity and affinity of the antibody for the target agent where higher affinities permit lower concentrations. Each working electrode was covered with the capture probe solution. The Petri dish was covered and incubated at room temperature for 10-90 minutes depending on the antibody concentration. At the end of the incubation, the sensor chip was rinsed with de-ionized water, dried with nitrogen, and placed back in the Petri dish.

The working electrode or all three electrodes of each sensor with were covered with 1 M ethanolamine and the Petri dish covered. The sensor chip was incubated at room temperature for 15 min. At the end of this ethanolamine incubation, the sensor chip was rinsed with de-ionized water, dried with nitrogen, placed back in the Petri dish, and stored in a dry condition in an atmosphere of nitrogen at room temperature.

Over each working electrode, a target solution that may contain the target agent was placed onto each of the working electrodes. A lightly damp filter paper was placed in the Petri dish under the sensor chip to prevent the sample from drying out and the Petri dish was covered. The target solution was incubated for 5-30 minutes depending on the concentration of the target agent. For instance, the target solution could be incubated for 30 min for pg/mL and 5 min for ng/mL and more. After the target solution incubation, the sensor chip was rinsed with de-ionized water, dried with nitrogen, and placed back in the Petri dish.

Each working electrode was covered with a signaling solution containing a biotin-conjugated monoclonal signaling antibody. The signaling solution was incubated for 5-30 min depending on the target concentration, rinsed with de-ionized water, and dried with nitrogen. Each working electrode was covered with a reporter solution having a streptavidin-HRP conjugate. The reporter solution was incubated at room temperature for 30 min, rinsed with de-ionized water and dried with nitrogen.

A 3,3',5,5'-tetramethylbenzidine substrate (TMB substrate) was removed from the refrigerator and placed into a clean trough covered with aluminum foil. The chip was rinsed with DI water and dried with nitrogen. All three electrodes on each sensor were covered with the TMB substrate.

Figure 7:
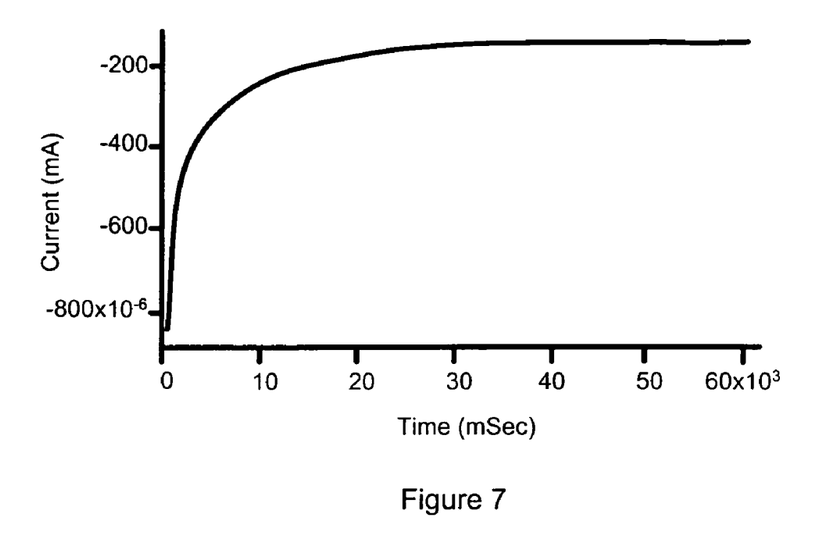
FIG. 7 shows experimental current versus time results for sixteen sensors on a sensor chip.
Figure 8:
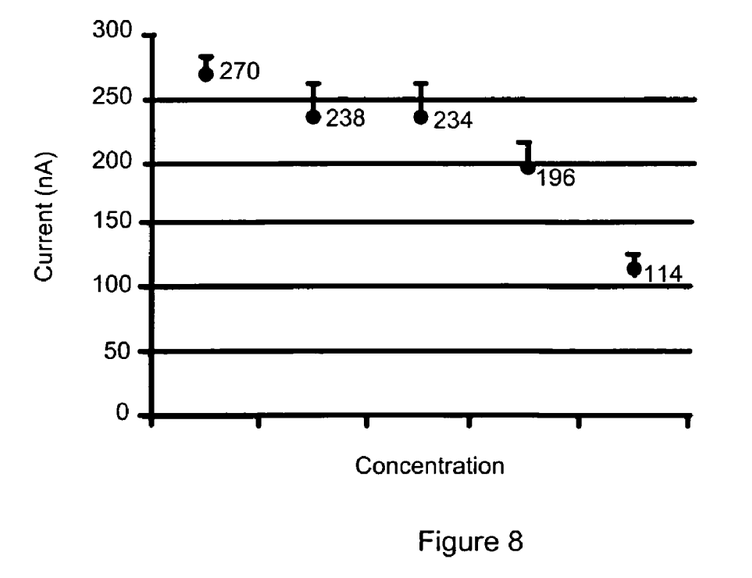
FIG. 8 shows the experimental current versus concentration results.

Amperometric measurements were performed at −150 mV and results are provided in FIG. 7 and FIG. 8. FIG. 7 shows the current versus time results for all 16 sensors on a chip. FIG. 8 shows the current versus the concentration of the target agent. The current is a function of the target agent concentration and can accordingly be used as an indicator of concentration.

As noted above, a chip can include a plurality of sensors. In some instances, the sensors are employed concurrently to test for the presence of different target agents. In many instances, testing for different target agents can employ different capture probes 44 and/or different signaling probes while employing the same reporter solution and the same mediator solution. As a result, a different sample solution is prepared for each target agent being tested. In some instances, different reporter solutions and/or mediator solutions can be employed for different target agents.

In some instances, different sensors on a chip are employed concurrently to test for the presence of the same different target agents. When the target agent originates from the same sample, different reporter solutions and/or mediator solutions can be employed with different sensors. In these instances, the results at one sensor can serve as a check on the results of another sensor. When the target agent to be tested is the same but originates from different samples, the sample solution prepared for use with each sensor is different.

Other embodiments, combinations and modifications of this invention will occur readily to those of ordinary skill in the art in view of these teachings. Therefore, this invention is to be limited only by the following claims, which include all such embodiments and modifications when viewed in conjunction with the above specification and accompanying drawings.

The invention claimed is:

1. An electrochemical sensor device, comprising:
   electrodes on a substrate, the electrodes including a working electrode, a reference electrode, and a counter electrode; and
   a self-assembly monolayer on the reference electrode, the self-assembly monolayer comprising 12-mercapto(8-biotinamide-3,6-dioxaoctyl)dodecanamide and 11-mercapto-1-undecanol.

2. The device of claim 1, wherein the 12-mercapto(8-biotinamide-3,6-dioxaoctyl)dodecanamide is bonded to streptavidin.

3. The device of claim 1, wherein the monolayer includes sulfur of the 12-mercapto(8-biotinamide-3,6-dioxaoctyl)dodecanamide linked directly to the reference electrode.

4. The device of claim 1, wherein the reference electrode consists of a single layer of metal selected from the group consisting of gold, silver, copper, platinum, chromium, aluminum, titanium, and nickel.

5. The device of claim 1, wherein the reference electrode consists of a single layer of gold.

6. The device of claim 1, wherein the reference electrode, the working electrode, and the counter electrode each consists of a single layer of metal selected from the group consisting of gold, silver, copper, platinum, chromium, aluminum, titanium, and nickel.

7. The device of claim 1, wherein the reference electrode, the working electrode, and the counter electrode each consists of a single layer of gold.

8. The device of claim 1, wherein the reference electrode and the counter electrode each have a shape that is different from a shape of the working electrode.

9. The device of claim 1, wherein the sensor occupies an area of $160\ \mu m^2$ to $25\ mm^2$.

10. The device of claim 1, wherein the reference electrode, the working electrode and the counter electrode each consist of a single layer of an electrically conducting material.

11. The device of claim 1, wherein the self-assembly monolayer is on the working electrode.

12. The device of claim 1, wherein the reference electrode is arranged about the perimeter of the working electrode such that a portion of the working electrode is positioned between different regions of the reference electrode.

13. The device of claim 1, wherein the counter electrode is arranged about the perimeter of the working electrode such that a portion of the working electrode is positioned between different regions of the counter electrode.

* * * * *

UNITED STATES PATENT AND TRADEMARK OFFICE
CERTIFICATE OF CORRECTION

PATENT NO. : 8,329,010 B2 Page 1 of 1
APPLICATION NO. : 12/154971
DATED : December 11, 2012
INVENTOR(S) : Jen-Jr Gau It is certified that error appears in the above-identified patent and that said Letters Patent is hereby corrected as shown below:

On the title page item (73) Assignee, please delete "Kotura, Inc." and insert --GeneFluidics, Inc.--.

Signed and Sealed this
Ninth Day of July, 2013

Teresa Stanek Rea
*Acting Director of the United States Patent and Trademark Office*